United States Patent [19]
Edel et al.

[11] Patent Number: 4,595,365
[45] Date of Patent: Jun. 17, 1986

[54] METHOD OF AND APPARATUS FOR CLEANING TEETH

[76] Inventors: Alan Edel; Julian Edel; Edgar Asher, all of 19 Keren Kayemet St., Petach, Tikva, Israel

[21] Appl. No.: 672,487

[22] Filed: Nov. 16, 1984

[30] Foreign Application Priority Data

Nov. 21, 1983 [IL] Israel .................................. 70281

[51] Int. Cl.⁴ .................................................. A61C 3/02
[52] U.S. Cl. ........................................ 433/216; 433/88
[58] Field of Search ................ 433/88, 80, 125, 216; 51/439, 427

[56] References Cited

U.S. PATENT DOCUMENTS

| | | | |
|---|---|---|---|
| 783,218 | 2/1905 | Murray | 51/439 |
| 822,379 | 6/1906 | Luckenbach | 51/439 |
| 2,325,517 | 7/1943 | Howard | 51/439 |
| 4,214,871 | 7/1980 | Arnold | 433/88 |
| 4,253,610 | 3/1981 | Larkin | 51/439 |
| 4,412,402 | 11/1983 | Gallant | 433/88 |
| 4,462,803 | 7/1984 | Landgraf et al. | 433/125 |

FOREIGN PATENT DOCUMENTS 1072767 9/1954 France .............................. 433/88

Primary Examiner—John J. Wilson
Attorney, Agent, or Firm—McAulay, Fields, Fisher, Goldstein & Nissen

[57] ABSTRACT

An apparatus is provided having a chamber in which two streams are mixed, one stream comprising a liquid, such as water, under pressure, and the other comprising a mixture of a gas, such as air, under pressure, along with an abrasive material which is soluble in the liquid. Mixing of the two streams is completed in the chamber and a single stream exits from the chamber to be directed against a tooth surface to be cleaned. The surfaces of teeth are cleaned employing the single jet issuing from the nozzle of the chamber, the jet comprising the mixture of the liquid, gas, and liquid soluble abrasive material.

5 Claims, 2 Drawing Figures

METHOD OF AND APPARATUS FOR CLEANING TEETH

BACKGROUND OF THE INVENTION

The use of mixtures of fluids and abrasive solids for cleaning of surfaces is well known. Mixtures of high pressure fluids, including both liquids and gases, with abrasive particles, such as sand, are described, for example, in U.S. Pat. No. 794,122, Rosengarten; U.S. Pat. No. 2,071,472, Pletcher; U.S. Pat. No. 2,290,979, Luce; U.S. Pat. No. 2,234,250, Voerge; U.S. Pat. No. 2,325,517, Howard; and U.S. Pat. No. 2,376,616, Oechsle et al. In the last referenced patent, two separate streams are fed, one of a sand air mixture and the other of water, the two mixing before joining the surface to be cleaned. Similarly, sand is mixed with a fluid and directed against a surface to be cleaned in U.S. Pat. No. 783,218, Murray; U.S. Pat. No. 3,646,709, Nolan; U.S. Pat. No. 3,690,067, Goss et al; U.S. Pat. No. 3,828,478, Bemis; U.S. Pat. No. 3,276,168, Ashworth; U.S. Pat. No. 3,994,097, Lamb; and U.S. Pat. No. 4,369,607, Bruggeman et al.

The mixture of an abrasive with a fluid for cleaning of teeth has also been described in the prior art. For example, in U.S. Pat. No. 3,971,136, Madsen an insoluble abrasive is mixed with water and air and delivered against the surface of teeth to clean them. More recently, water soluble abrasives have been employed for the cleaning of teeth, and such soluble abrasives are believed to be advantageous because they avoid excess abrasion of the tooth enamel. For example, U.S. Pat. No. 4,214,871, Arnold shows the use of halite, in combination with water, but with no gaseous component, to clean teeth.

Water soluble abrasives have also been used for cleaning of teeth, in combination with water and a gas stream, for example, in U.S. Pat. Nos. 4,174,571 and 4,412,402, both listing Gallant as the inventor. In each of these patents, however, the water stream and the abrasive laden gas stream are delivered from separate nozzles and are mixed only at some point between their ejection from the nozzle and the surface of the tooth to be cleaned. As a consequence, even when the nozzle delivering the water stream and the nozzle delivering the abrasive laden gas stream are formed as part of a single hand piece, the distance that this hand piece must be held from the surface of the teeth to be cleaned is critical, or the two streams do not mix adequately.

BRIEF DESCRIPTION OF THE INVENTION

In accordance with the present invention, a hand piece for a device to remove plaque from a tooth surface and polish that surface is provided, the hand piece being provided with means to supply a stream of liquid, such as water, under pressure, and a means to supply a stream of gas, such as air, under pressure. The gas stream supplied entrains an abrasive powder which is soluble in the liquid. The two fluid streams enter a single chamber where they are sufficiently mixed to provide a homogeneous mixture, and this homogeneous mixture is ejected from a single nozzle, under the pressure provided by the fluid streams, to be directed against a tooth surface.

Because the homogeneous mixing of the two streams is accomplished prior to ejection from a nozzle, the teeth may be effectively cleaned without concern as to a critical distance between the nozzle hand piece and the surface of the tooth. This is by way of distinction from the prior art systems where two separate nozzles are provided so that two streams must be mixed on their way to the tooth surface from the nozzles. Thus, the insufficient cleaning action which frequently results from the use of the tooth, itself, as the mixing area is avoided, as is the waste of excess amounts of abrasive powder.

It is thus an object of the present invention to improve the method of cleaning teeth with an abrasive laden gas and water.

It is a further object of the invention to provide a method of cleaning teeth comprising mixing an abrasive laden gas with a stream of water and directing the mixed stream against a tooth to be cleaned from a single nozzle.

It is a still further object of the present invention to provide a dental hand piece in which an abrasive laden gas stream and a stream of water can be mixed for delivery of the mixture against the surface of the tooth to be cleaned.

DESCRIPTION OF THE PREFERRED EMBODIMENTS

Figure 1:
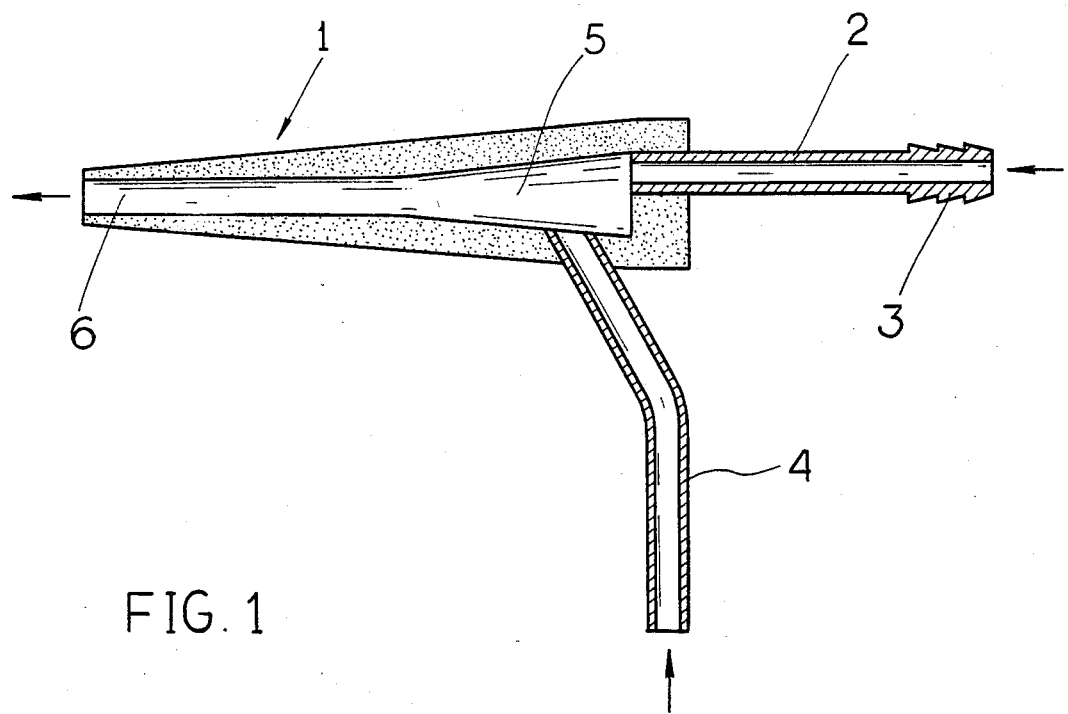
FIG. 1 is a sectional view of a dental hand piece in accordance with the present invention and FIG. 2 is an environmental view showing the hand piece of the present invention employed for the cleaning of tooth surfaces.

Referring to the drawings, and particularly to FIG. 1, a dental hand piece 1 is illustrated having a first end 2 which is adapted for connection to a source of abrasive laden gas. Preferably, the gas fed through this inlet is a mixture of air and an abrasive material, preferably water soluble, for cleaning of tooth surfaces. The inlet 2, as illustrated, has a stepped end 3 which is adapted for attachment to a flexible tubular member, though the means of connection of the inlet to the source of abrasive laden gas is not critical to the present invention.

Also attached to the dental hand piece 1 is a second inlet 4. Through this second inlet 4, a liquid, particularly water, enters the dental hand piece 1. The abrasive laden gas from inlet 2 and the water from inlet 4 mix in chamber 5 to form a homogeneous mixture of the water, air, and water soluble abrasive.

Figure 2:
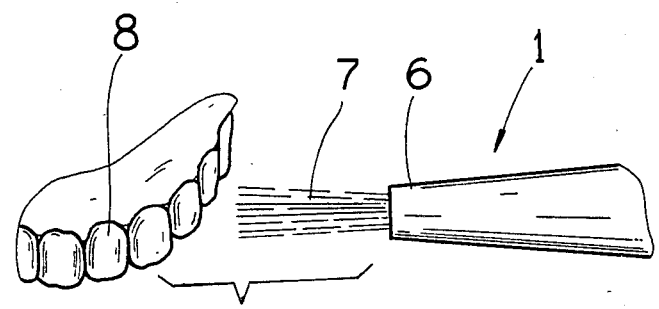

The force created by the pressure of the water and the gas forces the homogeneous mixture formed in chamber 5 through nozzle 6 to be directed against the tooth surfaces to be cleaned. As illustrated in FIG. 2, the stream 7 exiting from nozzle 6 is directed against the tooth surface 8 to be cleaned.

In theory, prior to the present invention, it might have been expected that the mixing of the water soluble abrasive and water in the chamber 5 would lead to premature dissolution of this water soluble abrasive. However, by properly sizing the chamber and controlling the pressures of the fluids entering it, the solution of the abrasive material is such as to provide an appropriate cleaning and polishing action on the tooth surface.

The mixing chamber and flow and pressure rates are sufficient to effect a homogeneous mixture of the abrasive laden gas stream and the liquid stream prior to emission from the nozzle 6. As an example, with a water pressure of from 10 to 50 psi and an air pressure of approximately 1 to 3 atmospheres, when the length of the chamber 5 is 8.0 mm., the large end of the chamber (adjacent the fluid entry points) is 2.5 mm., and the small end of the mixing chamber 5 (adjacent the nozzle) is 1.0 mm., an appropriate homogeneous mixing of the various streams is attained. This provides turbulent mixing of the liquid and abrasive laden gas so as to initiate solution of the abrasive particles prior to emission from the nozzle 6, without a sufficient dissolution to reduce the cleaning action on the tooth surface.

Because of the homogeneous mixing of the abrasive laden gas stream and the water stream in the chamber 5, the mixture exiting from the nozzle 6 is constant, and the intensity of the cleaning action on the tooth surface 8 is varied only by the change in distance between the nozzle 6 and the tooth surface 8. This distance, however, is not critical, in view of the homogeneous mixing action obtained in the chamber 5. The dentist, or dental hygienist, handling the dental hand piece 1 can control the space between the dental hand piece 1 and the tooth surface 8 in accordance with the cleaning action desired; however, some cleaning action is always obtained.

The abrasive powder employed in the abrasive laden gas stream which enters through the entry point 2 is, preferably, sodium bicarbonate. If desired, a flow facilitator, such as magnesium trisilicate can be mixed with the sodium bicarbonate. Other flow facilitators, such as tribasic calcium phosphate can also be used, with ratios as known in the art.

In accordance with the present invention, an apparatus and method for the mixing and delivery of a liquid and an abrasive laden gas stream have been shown. Contrary to the prior art, a homogeneous mixture of these streams is formed in a mixing chamber and the combination is delivered as a single stream to the tooth surface to provide the necessary cleaning action. While the abrasive employed is water soluble, because of the pressures and mixing chamber configuration, the mixing is such as to only create a homogeneous mixture, without full dissolution of the abrasive material. Further, because the streams have already been mixed, there is no critical distance between the nozzle from which the homogeneous mixture exits and the tooth surface to be cleaned.

The invention should not be considered as limited, except as set forth in the appended claims.

We claim:

1. A method for cleaning and polishing teeth employing a water soluble abrasive powder material comprising:
   a. homogeneously mixing in a dental hand piece an abrasive laden gas stream and a liquid stream in which said abrasive is soluble without full dissolution of said abrasive;
   b. directing said homogeneous mixture from said dental hand piece as a single stream; and
   c. directing said single stream against the surface of a tooth to be cleaned.

2. The method of claim 1 wherein said gas is air.

3. The method of claim 1 wherein said liquid is water.

4. The method of claim 3 wherein said abrasive is sodium bicarbonate.

5. The method of claim 1 wherein said gas pressure is in the range of 1 to 3 atmospheres and the water pressure is in the range of 10 to 50 psi.

* * * * *